United States Patent [19]
Damia

[11] Patent Number: 5,464,043
[45] Date of Patent: Nov. 7, 1995

[54] PRESSURE ADJUSTMENT VALVE FOR CIRCUITS FOR THE MANUAL ADMINISTRATION OF GAS MIXTURES IN THE MEDICAL FIELD

[75] Inventor: Giorgio Damia, Milan, Italy

[73] Assignee: Dar Societa' per Azioni, Mirandola, Italy

[21] Appl. No.: 225,292

[22] Filed: Apr. 8, 1994

[51] Int. Cl.⁶ .................................................. F16K 37/00
[52] U.S. Cl. ................................. 137/614.2; 137/556.6; 251/65; 251/904
[58] Field of Search .................. 137/529, 599.1, 137/614.2, 556.6; 251/65, 904, 208, 209

[56] References Cited

U.S. PATENT DOCUMENTS

| | | | |
|---|---|---|---|
| 2,514,025 | 7/1950 | Bush | 137/556.6 |
| 2,597,952 | 5/1952 | Rosenlund | 251/65 |
| 3,409,270 | 11/1968 | Hulsey | 251/209 |
| 4,026,284 | 5/1977 | Boehringer | 137/614.2 |
| 4,143,872 | 3/1979 | Havstad et al. . | |
| 4,183,499 | 1/1980 | Swartz et al. | 251/208 |
| 4,654,027 | 3/1987 | Dragan et al. | 137/614.2 |
| 4,750,707 | 6/1988 | Johncox et al. | 251/904 |
| 4,918,768 | 4/1990 | DeSousa et al. | 251/209 |

FOREIGN PATENT DOCUMENTS

| | | | |
|---|---|---|---|
| 0411714 | 2/1991 | European Pat. Off. . | |
| 17534 | 7/1913 | France | 134/614.2 |
| 2153360 | 5/1973 | France . | |
| 21635 | of 1906 | United Kingdom | 251/208 |
| 8600682 | 1/1986 | WIPO . | |

OTHER PUBLICATIONS

William W. Mushin et al. "Automatic Ventilation of the Lungs" 1980 Blackwell Scientific Publ., Oxford, p. 735, lines 6–14, figs. 79.3; p. 744, lines 38–41.
Database WPI, Week 9145, Derwent Publ. Ltd., London, GB; AN 91–331499, Zaikin V G "Breathing exercise device . . ." & SU-A-1632430 (Kuib Aviation Inst) 7 Mar. 1991 abstract.

Primary Examiner—A. Michael Chambers
Attorney, Agent, or Firm—David A. Hey

[57] ABSTRACT

The present invention relates to pressure adjustment valves for circuits for the manual administration of gas mixtures in the medical field, such valves including a body that can be interposed on the circuit of a manual respiration unit and which has an intake port and a discharge port. Means are provided in the body of the valve which means can be positioned to vary the useful passage section of the gas stream within the valve in order to modify the resistance created by the adjustment valve to the gas steam.

7 Claims, 2 Drawing Sheets

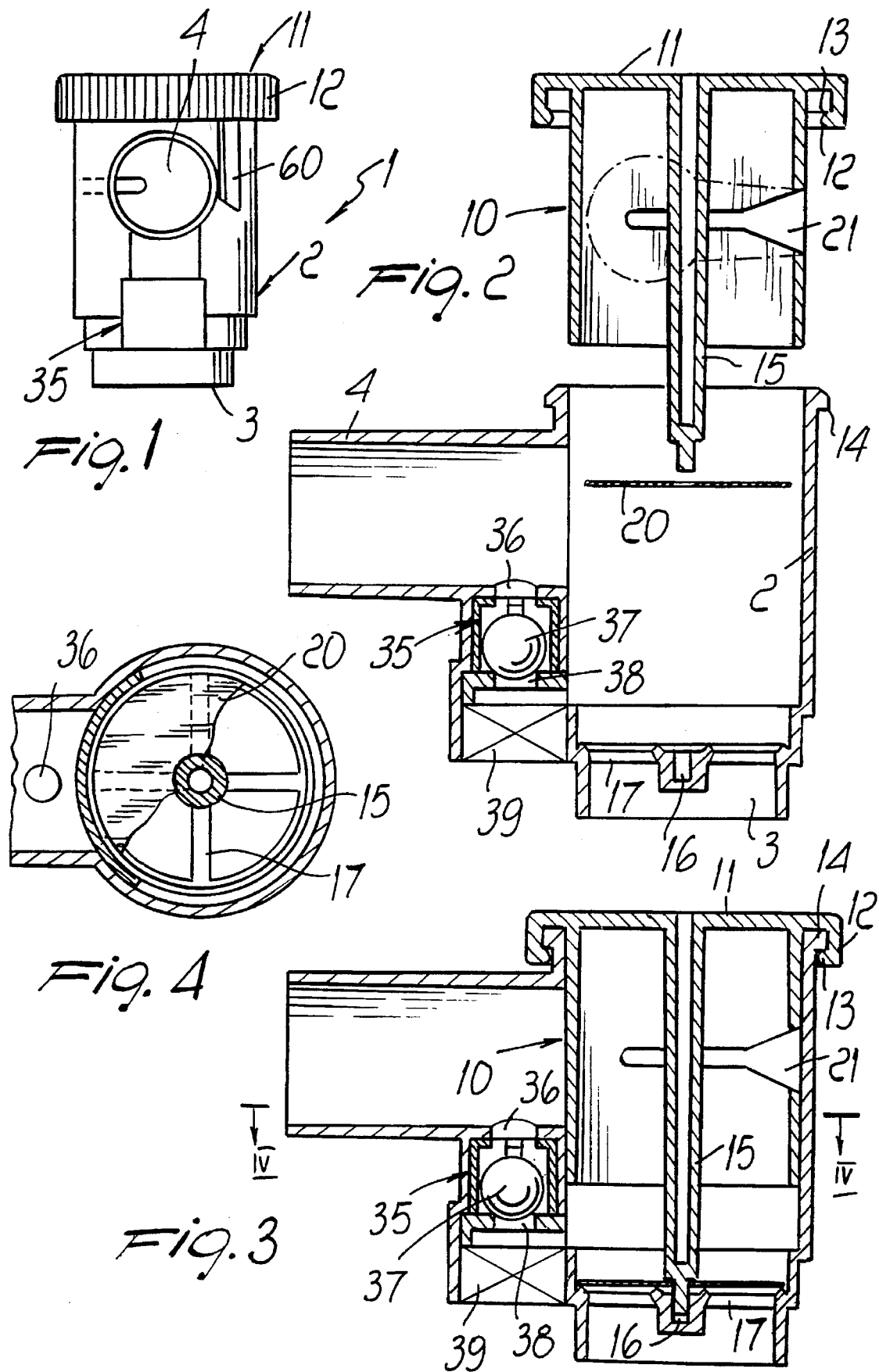

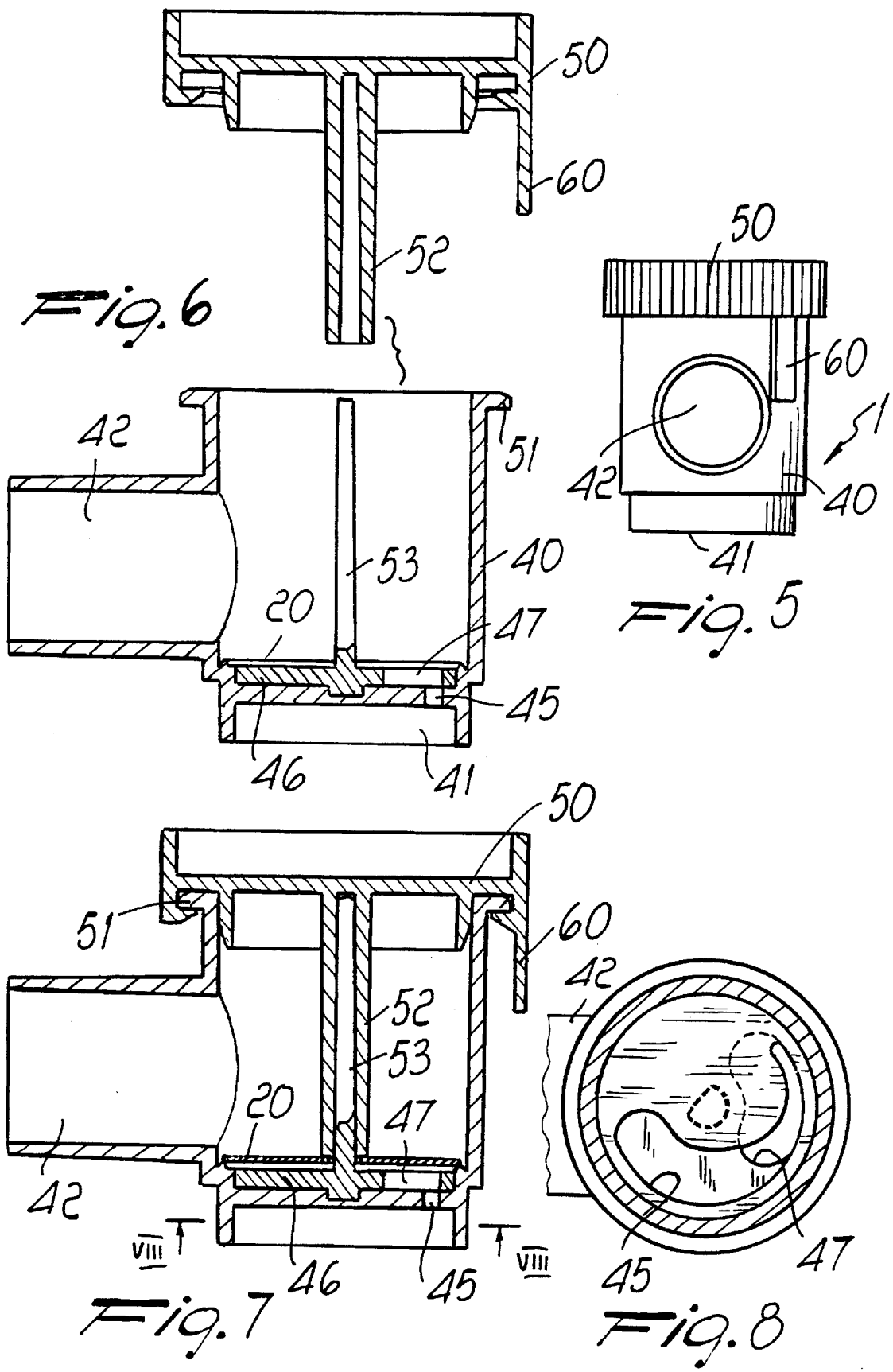

PRESSURE ADJUSTMENT VALVE FOR CIRCUITS FOR THE MANUAL ADMINISTRATION OF GAS MIXTURES IN THE MEDICAL FIELD

BACKGROUND OF THE INVENTION

The present invention relates to a pressure adjustment valve for circuits for the manual administration of gas mixtures in the medical field.

As it is known, throttling valves having the purpose of adjusting the pressure of the gas stream are currently used in circuits for the manual administration of gas mixtures in the medical field.

These valves, which are normally provided on a connector that mutually connects the manually-operated bag, the fresh-gas feed tube and the patient's connector, are currently comprised of a cylindrical body provided with intake and discharge ports for the required connections.

Pressure adjustment is generally performed on the intake port by means of a disk which is pushed by an adjustable spring so as to act both as check valve and as flow throttling element according to the setting of the spring.

These valves, in addition to being mechanically relatively complicated, are generally difficult to calibrate, due to the fact that calibration is performed by setting a spring, with the unavoidable expected errors. Furthermore, a moving disk often jams because of difficulties in the sliding of the disk and because secretions of the patient may reach the working area of the disk.

SUMMARY OF THE INVENTION

One object of the present invention is to solve the problems described above by providing a pressure adjustment valve for circuits for the manual administration of gas mixtures in the medical field which allows adjustment of the flow without using spring-loaded moving parts and without having to provide elastic calibration means.

A further object of the invention is to provide an adjustment valve that allows extremely precise adjustment which can be easily and quickly visualized, thus considerably facilitating such adjustment.

Another object of the present invention is to provide a pressure adjustment valve that, by virtue of its particular construction characteristics, is capable of giving the greatest assurances of reliability and safety during use.

A further object of the present invention is to provide a pressure adjustment valve for circuits for the manual administration of gas mixtures in the medical field that can easily be constructed from commonly commercially available elements and materials and which is competitive from a economic point of view.

These objects and others are provided according to the present invention, by a pressure adjustment valve for circuits for the manual administration of gas mixtures in the medical field which comprises a body that can be interposed on the circuit of a manual respiration unit and has an intake port and a discharge port, wherein the body includes an adjustment element that can be positioned so as to vary the useful passage section of the gas stream in order to modify the resistance created by the adjustment valve to the gas stream.

BRIEF DESCRIPTION OF THE DRAWINGS

FIG. 1 is a schematic elevation view of a first embodiment of the pressure adjustment valve according to the present invention.

FIG. 2 is an exploded sectional view of the adjustment valve according to the present invention.

FIG. 3 is a sectional view of the adjustment valve according to the present invention.

FIG. 4 is a sectional view, taken along the plane IV—IV of FIG. 3 of the adjustment valve according to the present invention.

FIG. 5 is an elevation view of a further embodiment of the pressure adjustment valve according to the present invention.

FIG. 6 is a exploded sectional view of the of the adjustment valve according to the present invention.

FIG. 7 is a sectional view of the of the adjustment valve according to the present invention.

FIG. 8 is a sectional view, taken along the plane VIII—VIII of FIG. 7 of the adjustment valve according to the present invention.

DESCRIPTION OF THE PREFERRED EMBODIMENTS

With reference to the above figures and particularly to FIGS. 1 to 4, the pressure adjustment valve for circuits for the manual administration of gas mixtures in the medical field, according to the present invention, generally designated by the reference numeral 1, comprises a cylindrical body 2 having an axial intake port 3 and a discharge port 4 that extends radially from the side wall of the body 2.

Inside said cylindrical body 2 it is possible to arrange an adjustment element advantageously comprised of a cylindrical skirt 10 that enters the body 2 and the outer wall of which is very close in size to the inner wall of the body 2. The skirt 10 is closed by a lid 11 that has a ridge or rim 12 provided with a tooth 13 for coupling to an annular protrusion 14 formed at the top of the cylindrical body 2, such that when tooth 13 and protrusion 14 are coupled, the skirt 10 and the cylindrical body 2 are firmly attached to each other but allow mutual rotation.

An axial stem 15 extends from the lid 11 of the skirt 10 and enters a centering seat 16 which is supported by a cross-shaped element 17 arranged at the inlet 3 of body 2.

A membrane 20 rests on the cross-shaped element 17 and forms a check valve.

The pressure adjustment valve 1 according to the present invention accomplishes pressure adjustment by varying the useful passage section, of the body 2. In particular, the radial surface of the skirt 10 includes a slot 21 that runs along the circumference of the skirt with a variable cross-section so that when skirt 10 is engaged with body 2, the slot 21 corresponds in lateral location to the discharge port 4 of body 2. Therefore, by varying the arrangement of the skirt 10 with respect to the cylindrical body 2, the arrangement of slot 21 is also varied with respect to discharge port 4 and therefore it is possible to vary the useful passage section of the adjustment valve 1. This variation creates a modification of the resistance of the adjustment valve 1 to the gas stream.

For example, the resistance increases when a narrower part of the slot 21 is arranged at the discharge port 4 and resistance decreases when a wider part of the slot 21 is arranged at the discharge port 4.

A safety bypass valve, generally designated by the reference numeral 35, is provided monolithically with the cylindrical body 2 and intervenes in case of overpressure. The bypass valve 35 is advantageously comprised of a branching port 36 which is provided on the discharge port 4 and below which there is a metal ball 37 retained on a connecting port or opening 38 both by its own weight and by the action of a permanent magnet 39. Only in case of overpressure can the ball 37 overcome the return action produced by its own weight and by the permanent magnet 39, freeing the opening 38 and thus providing bypass connection between the interior of the cylindrical body 2 and the discharge port 4, even if, for any reason, the normal connection with discharge port 4 is obstructed.

A further embodiment of the present invention is illustrated in FIGS. 5 to 8, wherein a cylindrical body, generally designated by the reference numeral 40, includes an axial intake port 41 and radial discharge port 42. An inlet 45 is formed through a wall defining the intake port 41 and is comprised of a bean-shaped opening following the circumference of the intake port 41.

A disk-like element 46 having an opening 47 with a circumferentially variable cross-section is rotatably mounted above the wall that defines the intake port 41 and forms the inlet 45. The useful air passage section of the adjustment valve 1 can be varied by changing the arrangement of the opening 47 with respect to the inlet 45.

Above the disk-like element 46 there is a membrane 20 that forms a check valve.

The cylindrical body 40 is closed by a plug like element 50 that couples in a snap-together manner to the upper edge 51 of the cylindrical body 40 and is provided with an axial stem 52 that rigidly and rotationally couples to a pivot 53 extending from the disk-like element 46 and thereby can be used to rotate the disk-like element 46 and change the arrangement of the opening 47 and inlet 45.

In use the useful passage section of the adjustment valve 1 can be varied by rotation of the plug 50 with respect to body 40. Such rotation in turn rotates the disk-like element 45 and causes a variation of the arrangement between the opening 47 and the inlet 45 which in turn acts to modify the resistance of the adjustment valve 1 to the gas stream. For example, the resistance increases when a narrower part of the opening 47 corresponds to the inlet 45 and resistance decreases when a wider part of the opening 47 corresponds to the inlet 45.

Referring to both embodiments above the plug-like element 50 and the lid 11 each have a notch, designated by the reference numeral 60, that extends axially and acts as a reference element to clearly indicate the mutual arrangement of the cylindrical body 2 or 40 with the plug 50 or lid 11, respectively. It is therefore easy to visualize which passage section is used, and to ascertain the amount of resistance to the gas flow.

As noted above, the pressure adjustment valve according to the present invention performs pressure adjustment by varying the useful flow passage of the valve. The various parts of the adjustment valves according to the present invention greatly reduce the likelihood of jammings and allow extremely precise adjustment to be performed.

In addition, the provision of an overpressure valve element directly integrated with the main valve body provides a further safety feature.

The invention thus conceived is susceptible to numerous modifications and variations, all of which are within the scope of the inventive concept.

All the details may furthermore be replaced with other technically equivalent elements.

In practice, the materials employed, as well as the contingent shapes and dimensions, may be adjusted according to the particular requirements of the practitioner.

What is claimed is:

1. A Pressure adjustment valve for circuits for the manual administration of gas mixtures in the medical field, comprising a body that can be interposed on the circuit of a manual respiration unit and having an inlet formed through a portion of a bottom wall of said body and a discharge port;

an adjustment element within said body which may be positioned relative to said body to vary the useful passage section of a gas stream passing through said adjustment valve and thereby modify resistance created by said adjustment valve to said gas stream;

wherein said adjustment element comprises a rotatable disk-like element which has an opening formed therethrough which runs along the circumference of said disk-like element, wherein said opening interacts with said inlet of said body to vary the useful air passage section of said adjustment valve; and a plug-like element having lid for rotatable connection to said body and a axial stem extending from said lid for rigid connection to said disk-like element;

wherein rotation of said plug-like element results in corresponding rotation of said disk-like element to adjust the arrangement of said opening of said disk-like element with said inlet of said body.

2. An adjustment valve according to claim 1, wherein said valve further includes a notch extending from said lid of said plug-like element which aids in visualization of the mutual arrangement of said adjustment element and said body.

3. A Pressure adjustment valve for circuits for the manual administration of gas mixtures in the medical field, comprising a body that can be interposed on the circuit of a manual respiration unit and having an intake port and a discharge port, said intake port including a cross-shaped element including a centering seat; and an adjustment element which may be inserted within said body and which may be positioned relative to said body to vary the useful passage section of a gas stream passing through said adjustment valve and thereby modify resistance created by said adjustment valve to said gas stream;

wherein said adjustment element comprises a cylindrical skirt said skirt including a lid portion, a side wall, and a slot which extends circumferencially along said side wall, said slot having a variable cross section; and wherein said slot of said adjustment element corresponds to said discharge port of said body in lateral relationship when said adjustment element is inserted within said body; and wherein an axial stem extends from the bottom of said lid of said skirt and said axial stem can be inserted into said centering seat supported by said cross-shaped element located as said intake port of said body.

4. An adjustment valve according to claim 3 wherein said lid has a ridge provided with a tooth for coupling to a corresponding annular protrusion formed at the top of said body.

5. An adjustment valve according to claim 4, wherein said valve further includes a check valve comprising a membrane supported by said cross-shaped element.

6. An adjustment valve according to claim 4, wherein said valve further includes a bypass valve formed monolithically with said body, said bypass valve comprising a ball arranged on a connecting opening that connects said discharge port to the interior of said body, and wherein said ball can be retained in position on said connecting opening by virtue of its own weight and by the action of a permanent magnet.

7. An adjustment valve according to claim 3, wherein said valve further includes a notch extending from said lid portion of said skirt which aids in visualization of the mutual arrangement of said adjustment element and said body.

* * * * *